United States Patent [19]

Hattler et al.

[11] Patent Number: 4,846,791
[45] Date of Patent: Jul. 11, 1989

[54] MULTI-LUMEN CATHETER

[75] Inventors: Brack G. Hattler; Irvin Furman, both of Denver, Colo.

[73] Assignee: Advanced Medical Technology & Development Corp., Denver, Colo.

[21] Appl. No.: 241,070

[22] Filed: Sep. 2, 1988

[51] Int. Cl.$^4$ ............................................. A61M 25/00
[52] U.S. Cl. ........................................ 604/43; 604/53; 604/158; 128/343
[58] Field of Search .................................. 604/43–65, 604/51–53, 158–170, 280–283; 128/343

[56] References Cited

U.S. PATENT DOCUMENTS

| | | | |
|---|---|---|---|
| 3,584,624 | 6/1971 | De Ciutiis | 604/170 X |
| 3,598,118 | 8/1971 | Warren | 604/53 |
| 4,180,068 | 12/1979 | Jacobsen et al. | 604/44 |
| 4,203,436 | 5/1980 | Grimsrud | 604/44 |
| 4,402,684 | 9/1983 | Jessup | 604/43 X |
| 4,738,658 | 4/1988 | Magro et al. | 604/280 X |

FOREIGN PATENT DOCUMENTS

592192  7/1925  France .............................. 604/44

Primary Examiner—Dalton L. Truluck
Attorney, Agent, or Firm—Dorr, Carson, Sloan & Peterson

[57] ABSTRACT

A multi-lumen catheter is formed by first introducing one end of an expandable tube into the blood vessel. A divider is then inserted into the distal end of the tube and extends the length of the tube, thereby dividing the tube into a plurality of the separate lumens. Insertion of the divider causes radial expansion of the tube which substantially seals the opening in the wall of the vessel. In one embodiment, the divider has a hollow triangular cross-section which creates four separate lumens. A series of raised protrusions extending outwardly from the sides of the divider prevent collapse of the tube against the divider.

24 Claims, 6 Drawing Sheets

MULTI-LUMEN CATHETER

BACKGROUND OF THE INVENTION

1. Field of the Invention

The present invention relates generally to the field of catheters, and in particular to catheters having multiple fluid carrying passageways.

2. Statement of the Problem.

Catheters of many types and configurations have been known and used for a number of years. Catheters function to carry fluids into and out from the blood vessel of a patient. One problem associated with catheters is the physical trauma and associated discomfort to the patient caused by insertion of the catheter and maintenance of the catheter in the patient for a period of time. Another problem associated with catheters is the risk of infection to the patient. These problems are multiplied when a number of catheters are inserted either at the same time or over a period of time. One approach to these problems has been to use a single catheter having multiple fluid carrying passageways, or lumens. This allows a number of different medications to be administered to the patient at one time using the same catheter.

A prior art search conducted by the inventor of the present invention disclosed a variety of multi-lumen catheters having various functions, as follows:

| Inventor | U.S. Pat. No. | Issue Date |
| --- | --- | --- |
| Hattler, et al. | 4,406,656 | 9-27-83 |
| Curelaru, et al. | 4,581,019 | 4-8-86 |
| Ekholmer | 4,717,379 | 1-5-88 |
| Luther | 4,668,221 | 5-26-87 |
| DeVries, et al. | 4,596,548 | 6-24-86 |
| Daugherty, et al. | 4,588,398 | 5-13-86 |
| Suzuki | 4,565,545 | 1-21-86 |
| Blake | 4,465,481 | 8-14-84 |
| Blake, et al. | 4,398,910 | 8-16-83 |
| Brown, et al. | 4,581,012 | 4-8-86 |

U.S. Pat. No. 4,406,656 issued to Hattler, et al., discloses on type of multi-lumen catheter in which a plurality of collapsible lumens are mounted around the periphery of a central flexible lumen that is capable of retaining its shape with or without fluid flow. Each collapsible lumen is capable of expanding when fluid is flowing therein to a much greater cross-sectional area than in its collapsed state.

U.S. Pat. No. 4,717,379 issued to Ekholmer discloses a catheter having a number of passages surrounding a central lumen. A series of perforations from these passages to the outside of the catheter enable a lubricant cream or gel stored in the passages to pass through the perforations and coat the surface of the catheter to ease insertion.

U.S. Pat. No. 4,668,221 issued to Luther pertains to the assembly of a stylet and catheter. A solid stylet is mounted through the catheter to enable more accurate piercing of the blood vessel, and to reduce the possibility of double piercing the vein. The catheter is made of a hydrophilic polymer which expands from the stylet after contacting body fluids. This permits the stylet to be withdrawn while leaving the catheter in place in the vein. The possibility of a plurality of lumens in the catheter is discussed.

U.S. Pat. No. 4,596,548 issued to DeVries, et al., pertains to a single lumen venous catheter to be inserted into the atrium of the heart. Externally placed ribs or dividers prevent the atrium of the heart from collapsing over the catheter opening to prevent blockage of the flow of blood into the catheter.

U.S. Pat. Nos. 4,581,019 issued to Curelaru, et al., 4,588,398 issued to Daugherty, et al., and 4,565,545 issued to Suzuki, all pertain to devices for insertion of single lumen catheters.

Finally, U.S. Pat. Nos. 4,398,910 and 4,465,481 issued to Blake, et al., and 4,581,012 issued to Brown, et al., relate generally to catheters having a plurality of lumens.

Solution to the Problem

None of the prior art references uncovered in the search set forth the use of a divider that is separately inserted into the catheter tube after the tube has been introduced into the blood vessel, thereby providing multiple lumens for the catheter. Absent the divider, the catheter tube can be fitted within a relatively small diameter hollow needle for insertion into the blood vessel. Introduction of the catheter tube into the blood vessel in this manner minimizes the size of the opening created through the wall of the blood vessel, and accordingly minimizes trauma and discomfort for the patient. Subsequent insertion of the divider radially expands the catheter tube and seals the opening in the blood vessel wall around the catheter tube. This minimizes leakage of blood from the vessel, and thereby reduces the risk of infection and hemorrhage.

SUMMARY OF THE INVENTION

This invention provides an improved multi-lumen catheter in which one end of an expandable tube is first introduced into a blood vessel through an opening in the wall of the blood vessel. A divider is subsequently inserted from the distal end of the tube and extends the length of the tube, thereby dividing the tube into a plurality of separate lumens. Insertion of the divider causes radial expansion of the tube and seals the opening between the tube and the wall of the blood vessel. This offers the advantages of requiring a smaller hole through the wall of the blood vessel, thus minimizing trauma, discomfort, and the risk of infection to the patient. These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 15b is a perspective view of the divider corresponding to FIG. 15a.

DETAILED DESCRIPTION OF THE INVENTION

Figure 4:
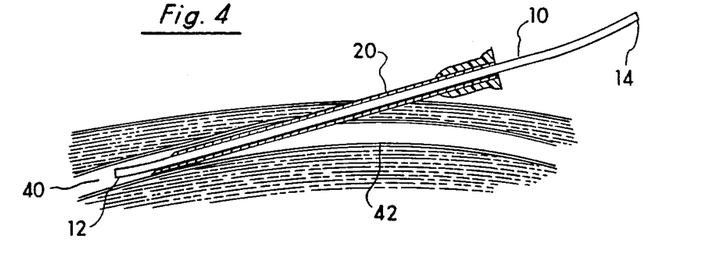
FIG. 4 is a side cross-sectional view showing the needle and catheter tube inserted into the blood vessel. This is the first step of the sequence shown in FIGS. 4 through 8 demonstrating installation of the present multi-lumen catheter.

FIGS. 4 through 8 illustrate the steps of installing a multi-lumen catheter in a blood vessel according to the present invention. FIG. 4 shows the first step in which the needle 20 and the end 12 of the catheter tube 10 are introduced into a blood vessel 40. The needle 20 punctures the wall 42 of the vessel and allows the end 12 of the catheter tube to be inserted through the needle into the interior of the blood vessel.

A conventional hollow stainless steel needle of the type commonly used in the medical field is satisfactory for inserting the catheter tube into the blood vessel. Needle sizes from 14 to 22 gauge are used depending upon the volume of the fluids involved. For example, larger diameters are necessary for central venous catheters. Smaller diameters are sufficient when dealing with smaller peripheral blood vessels.

The catheter tube is conventionally made of the flexible, expandable material such as amber latex, vinyl, or silicon rubber. The tube must have a proper outside diameter and rigidity to allow the tube to be slipped into the core of the needle with little or no restriction. The tube should have an outside diameter at least 0.005 inches smaller than the inside diameter of the insertion needle. The tube must also have sufficient flexibility to allow it to follow the natural curvature of the blood vessel.

Figure 5:
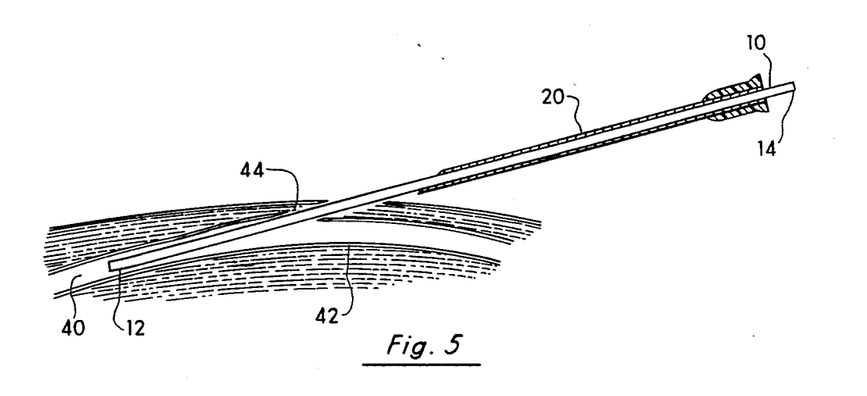
FIG. 5 is a side cross-sectional view showing retraction of the needle from inside the blood vessel, with the end of the catheter tube remaining inside the blood vessel.

Following insertion of the catheter tube, the needle 20 is then retracted out of the blood vessel, but the end of the catheter tube remains in place inside the blood vessel as shown in FIG. 5. Retraction of the needle leaves an annular opening 44 in the vessel wall 42 around the outside of the tube 10.

Figure 6:
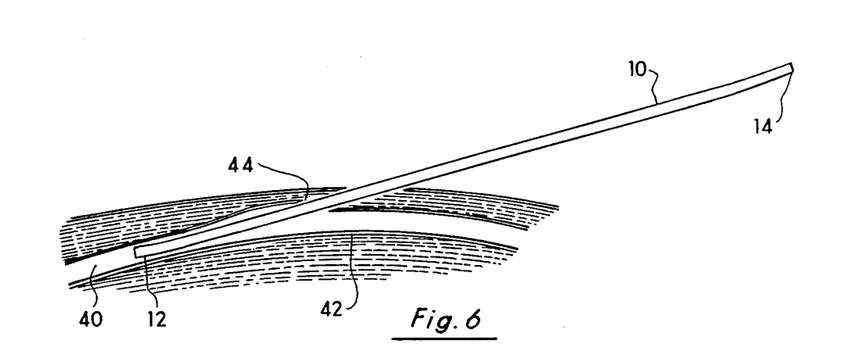
FIG. 6 is a side cross-sectional view showing removal of the needle from the catheter following catheter tube.

The next step is removal of the needle from the catheter tube as shown in FIG. 6. In one embodiment of the present invention, the needle is removed simply by sliding the needle back over the distal end 14 of the tube. Alternatively, a conventional "break away" needle can be employed that has lines of weakness or perforations extending the length of the needle. The needle readily separates into two halves along its major axis to facilitate removal from the catheter tube.

Figure 7:
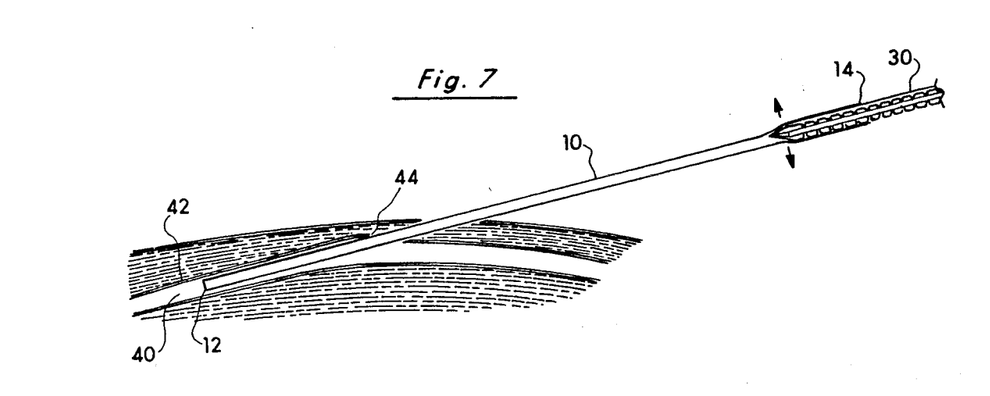
FIG. 7 is a side cross-sectional view showing initial insertion of the divider into the distal end of the catheter tube.

A divider 30 is then inserted into the catheter tube from the distal end 14 of the tube, as shown in FIG. 7, thereby dividing the tube into a plurality of separate lumens. Details of the preferred embodiment of the divider are illustrated in the perspective view of FIG. 1, in the side elevational view of FIG. 2, and in the front cross-sectional view of the divider and tube in FIG. 3. As the divider is inserted into the tube, each of the outer edges or corners 32 of the divider contact the inside surface of the tube to form a fluid-tight seal extending the length of the divider between adjacent lumens. In the preferred embodiment, the divider has a generally triangular, hollow cross-section. Three separate lumens 16 are created in the areas between the three sides 34 of the divider and the tube. A fourth, central lumen 36 is defined by the area within the divider.

Figure 8:
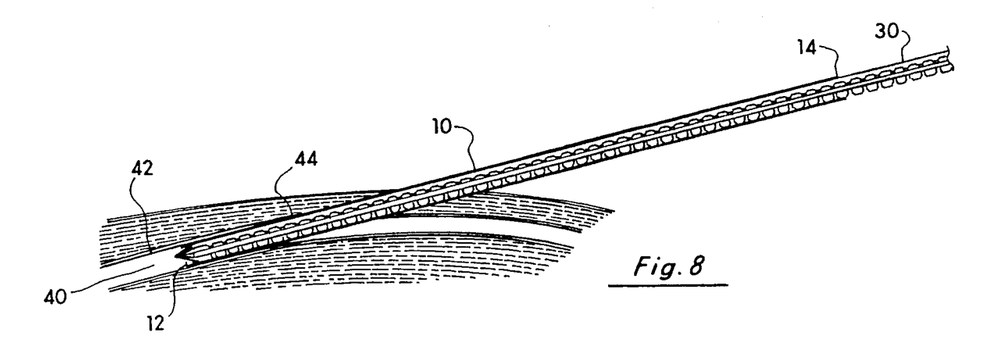
FIG. 8 is a side cross-sectional view showing complete insertion of a divider extending the length of the catheter tube, causing radial expansion of the tube to substantially seal the opening between the tube and the wall of the blood vessel.

The divider has cross-sectional dimensions slightly greater than the inside diameter of the catheter tube, thereby causing radial expansion of the tube as the divider is inserted, as shown in FIG. 7. FIG. 8 shows complete insertion of the divider 30 extending the entire length of the catheter tube 10. The cross-sectional dimensions of the divider should be selected with reference to the diameter of the needle 10 originally used to insert the catheter tube into the blood vessel. Ideally, insertion of the divider into the tube should result in sufficient radial expansion of the tube to substantially close and seal the annular opening 44 in the wall of the blood vessel around the outside of the tube. In other words, the ultimate outside diameter of the tube, with the divider inserted, is at least slightly greater than the inside diameter of the insertion needle, and is ideally as great as the outside diameter of the insertion needle. Catheters vary widely in diameter, depending upon the specific application and the diameter of the blood vessel involved. However, in most cases, a relatively small radial expansion of the tube of approximately 0.005 to 0.010 inches will be sufficient to substantially seal the annular opening 44 in the wall of the blood vessel.

The divider can be made of nylon, teflon, or some other material having adequate anti-friction properties to allow easy insertion of the divider into the tube. The material selected must have adequate flexibility so that the combination of the tube and divider can follow the natural curvature of the blood vessel without causing undue trauma or discomfort to the patient. The divider material must also have sufficient memory to retain its desired shape following insertion into the tube.

Figures 1, 3:
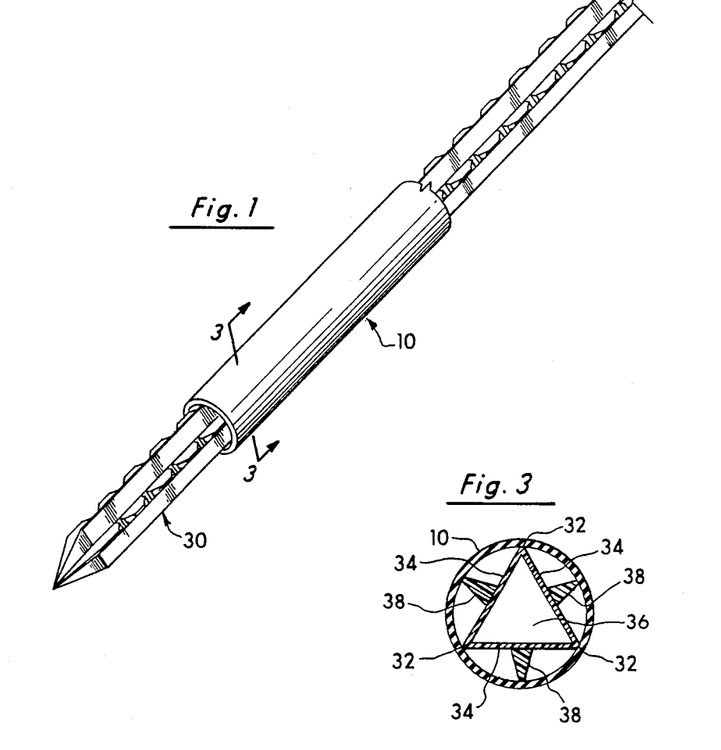
FIG. 1 is a perspective view showing the divider inserted through a catheter tube.
FIG. 3 is a front cross-sectional view of the divider inserted into the catheter tube.
Figure 2:
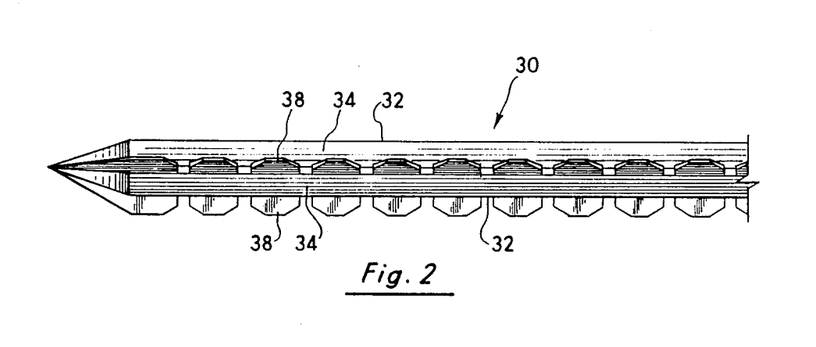
FIG. 2 is an side elevational view of the divider.

Blood pressure within the vessel will tend to cause the tube to collapse against the sides of the divider unless the internal pressure of the peripheral lumens is at least as great as the external blood pressure. Collapse or substantial constriction of these peripheral lumens would interfere with effective administration of medication to the patient through the catheter. To avoid this problem, support means extend between the inside surface of the tube and the sides of the divider to maintain a minimum spacing between the tube and each of the sides of the divider. In the preferred embodiment of the present invention, these support means are in the form of a series of raised protrusions extending axially along the mid-line of each of the sides of divider as shown in FIGS. 2 and 3. Other embodiments of the divider may not require these protrusions due to the geometry of the divider. For example, the cross-shaped and starshaped dividers shown in FIGS. 13-14 and 16-17 are unlikely to allow collapse or substantial constriction of the lumens within the catheter tube.

Following completion of the insertion process, the distal ends of the catheter tube and divider are removably attached to a distribution block of conventional design (not shown), which provides fluid communication for each of the separate lumens of the catheter with appropriate I.V. tubing and flow control devices for the respective fluids to be administered to the patient. Separate fluids and flow rates can be provided through each of the lumens of the catheter without mixing. The volumetric flow of the respective fluids to be administered to the patient can be controlled either by flow control devices associated with the distribution block, by providing different cross-sectional areas for various lumens, or by using more than one of the lumens for a given fluid.

The expandable nature of the catheter tube allows the cross-sectional area of each lumen to expand under the pressure of fluid flowing through the lumen, and to return to a substantially smaller cross-section when not in use. This feature is discussed in greater detail in U.S. Pat. No. 4,406,656.

Figures 9, 9A, 10, 10A:
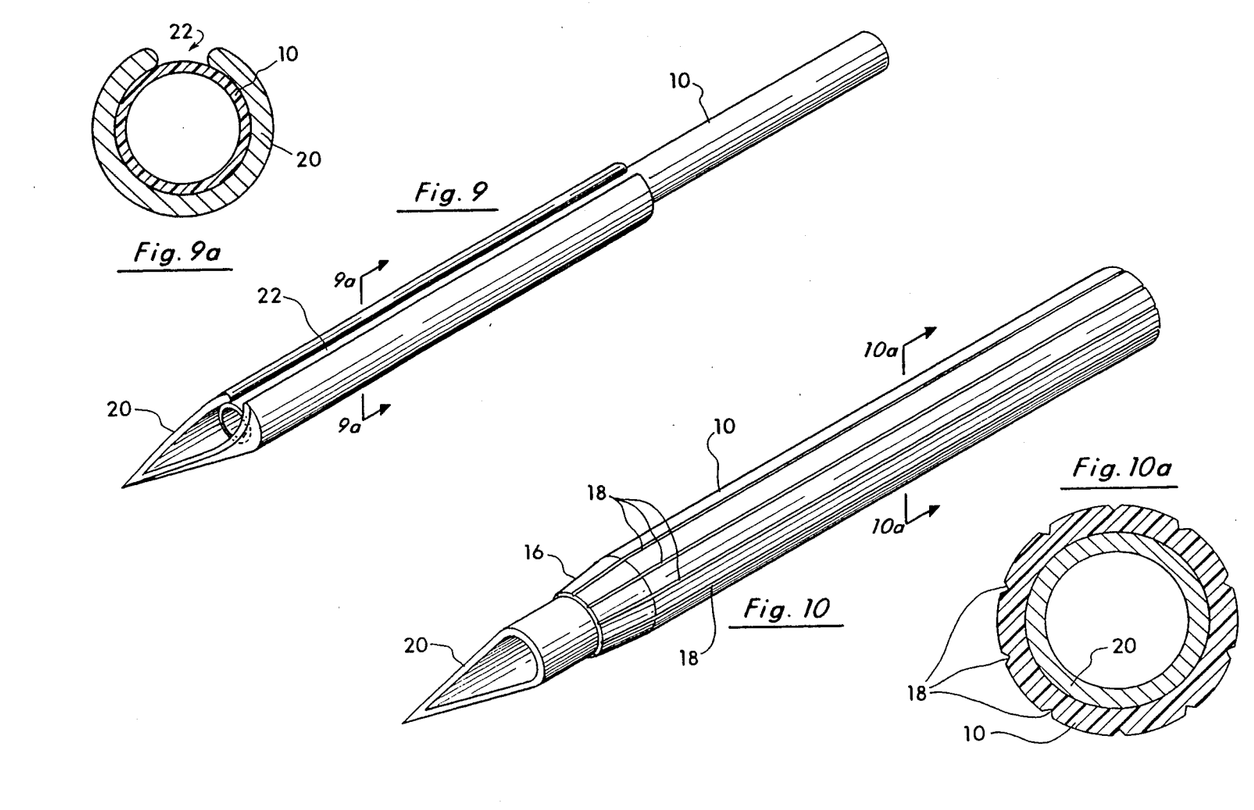
FIG. 9 is a perspective view showing an alternative embodiment of the present invention, in which a hollow needle having a slit extending its entire length is used to introduce the catheter tube into the blood vessel.
FIG. 9a is a cross-sectional view corresponding to FIG. 9.
FIG. 10 is a perspective view of an alternative embodiment of the present invention in which the catheter tube is a sleeve that fits over the insertion needle.
FIG. 10a is a cross-sectional view corresponding to FIG. 10.

FIGS. 9 and 9a show an alternative embodiment of the present invention in which the insertion needle 20 has a slit 22 extending axially along its entire length. This insertion process entails first piercing wall of the blood vessel with the tip of the needle 20. The end of the catheter tube 10 inside the needle is carried into the interior of the blood vessel with the needle. The needle 20 is then retracted from within the vessel by sliding the needle back over the catheter tube 10, while leaving the end of the catheter tube in the blood vessel. The needle 20 is subsequently removed from the catheter tube 10 be slipping the tube through the slit 22 extending along the length of the needle. The width of this slit is such that the catheter tube 10 can be removed from inside the needle through the slit with minimal effort following insertion of the catheter tube into the blood vessel. However, the width of the slit must not be so large that the catheter tube falls out of the needle prior to completion of the insertion process. The optimal dimension for the width of the slit 22 will depend upon the elasticity of the catheter tube and the thickness of the catheter tube wall. In general, the width of the slit will be approximately twice the thickness of the catheter tube wall. A greater width may be necessary if the catheter tube is too inelastic to be readily collapsed to fit through the slit. On the other hand, a highly elastic catheter tube can be axially stretched to temporarily reduce its wall thickness, and thereby fit through a narrower slit in the needle.

FIGS. 10 and 10a show another alternative embodiment of the present invention in which the catheter tube 10 is a sleeve that fits over the needle 20 prior to insertion. The needle inside the catheter tube is used to pierce the wall of the blood vessel. The beveled leading edge 16 of the catheter tube 10 allows the tube to be carried into the interior of the blood vessel with the needle. The needle is then withdrawn from inside the vessel and removed from the catheter tube 10. This is accomplished by pulling backward on the distal end of the needle which extends out of the distal end of the catheter tube, while holding the catheter tube 10 stationary so that the beveled end 16 of the tube remains in the blood vessel. Insertion of the divider into the catheter tube is then completed as discussed above. Thus, radial expansion of the catheter tube in this embodiment is required both for initial insertion of the needle 20 into the tube prior to insertion into the vessel, and for subsequent insertion of the divider into the catheter tube. The catheter tube 10 has a number of grooves 18 scored longitudinally along its exterior surface to facilitate this radial expansion of the catheter tube. If necessary, a separate elastic liner (not shown) located within the catheter tube can be employed to prevent rupture of the catheter tube in the event the grooves break apart during the insertion process.

Figure 11:
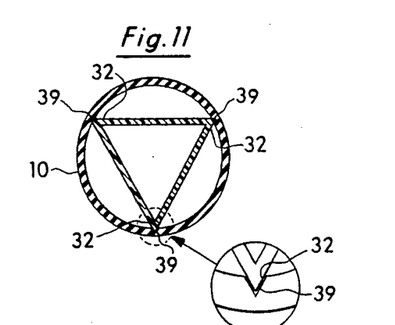
FIG. 11 is a cross-sectional view of the catheter tube and divider in an alternative embodiment of the present invention in which a series of recessed grooves extending along the inner surface of the catheter tube act as guides for the edges of the divider.

FIG. 11 shows an alternative embodiment of the present invention in which a series of recessed grooves 39 extend along the interior surface of the catheter tube 10. The number and placement of the grooves correspond to the number and placement of the edges of the divider. During insertion of the divider into the tube, the edges or corners 32 of the divider are guided by these grooves. This eases insertion of the divider and helps insure a better seal between the edges of the divider and the catheter tube.

Figure 12:
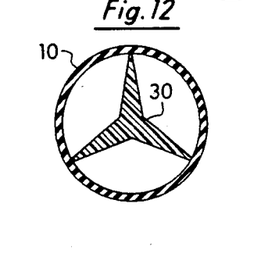
FIG. 12 is a cross-sectional view of the catheter tube and divider in an alternative embodiment of the present invention in which the divider has a generally Y-shaped cross-section to create three lumens within the catheter tube.
Figure 13:
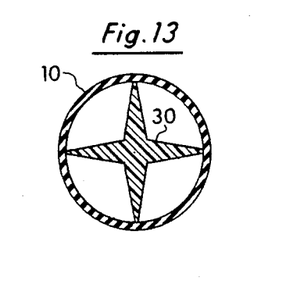
FIG. 13 is a cross-sectional view of the catheter tube and divider in an alternative embodiment of the present invention in which the divider has a solid, cross-shaped cross-section to create four lumens within the catheter tube.
Figure 14:
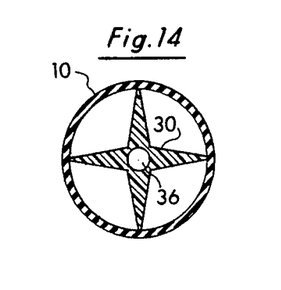
FIG. 14 is a cross-sectional view of the catheter tube and divider in an alternative embodiment of the present invention in which the divider has a hollow, cross-shaped cross-section to create five lumens within the catheter tube.
Figure 16:
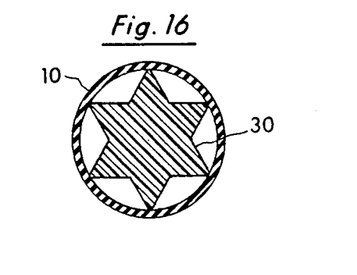
FIG. 16 is a cross-sectional view of the catheter tube and divider in an alternative embodiment of the present invention in which the divider has a solid, star-shaped cross-section to create six lumens within the catheter tube.
Figure 17:
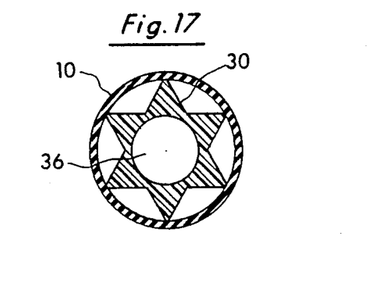
FIG. 17 is a cross-sectional view of the catheter tube and divider in an alternative embodiment of the present invention in which the divider has a hollow, star-shaped cross-section to create seven lumens within the catheter tube.

Although the divider is illustrated as being triangular is cross-section, any member of the general class of polygons can be utilized, such as a square, rectangle, diamond, pentagon, or hexagon. The divider can also be either hollow or solid. The divider can alternately have a Y-shaped, cross-shaped, or star-shaped cross section, as shown in FIGS. 12, 13, and 16. In addition, the divider can either be solid, or have a hollow cross-section to provide an additional central lumen formed within the divider, as shown in FIGS. 14 and 17.

Figure 15A:
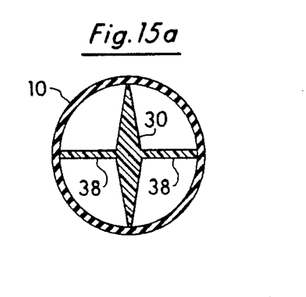
FIG. 15a is a cross-sectional view of the catheter tube and divider in an alternative embodiment of the present invention in which the divider is essentially a vertical bar that divides the catheter tube into two lumens. A series of raised protrusions extend outward from the midline of both faces of the divider to prevent collapse of the catheter tube against the faces of the divider.
Figure 15B:
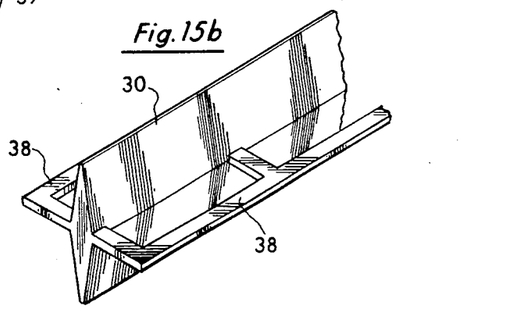

FIGS. 15a and 15b show a divider 30 in the form of a vertical bar that divides the catheter tube into two separate lumens. A series of raised protrusions 38 extend longitudinally along the midline of both faces of the divider to prevent collapse of the catheter tube against the sides of the divider.

Figure 18:
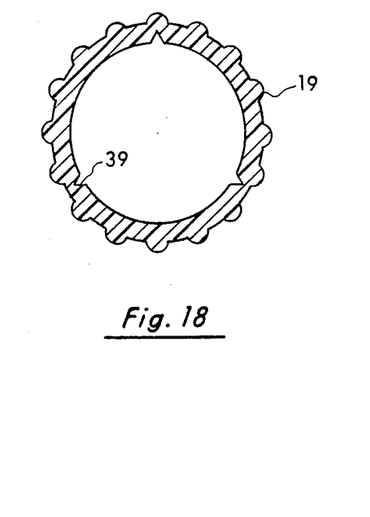
FIG. 18 is a cross-sectional view of an alternative embodiment of the catheter in which a series of recessed grooves extend along the inner surface of the catheter, and a series of raised ridges extend longitudinally along the outer surface of the catheter tube.

FIG. 18 is a cross-sectional view of another alternative embodiment of the present invention in which recessed grooves 39 extend along the inside surface of the catheter tube to guide insertion of the divider as discussed above and shown in FIG. 11, and which also has a number of raised ridges 19 extending longitudinally along the exterior of the catheter tube. These raised ridges serve to reduce the surface area of the tube in contact with the insertion needle an with the wall of the blood vessel. This minimizes friction and reduces the amount of force necessary for insertion of the catheter tube.

The above disclosure sets forth a number of embodiments of the present invention. Other arrangements or embodiments, not precisely set forth, could be practiced under the teachings of the present invention and as set forth in the following claims.

We claim:

1. A multi-lumen catheter comprising:
   (a) a tube, said tube being radially expandable from a first state with a first inner radius, to a radially expanded second state with a second larger inner radius;
   (b) means for selectively expanding said tube from said first state to said radially expanded second state, said expanding means including an insertable divider having a radius greater than said first inner radius and substantially equal to said second inner radius, insertion of said divider thereby dividing said tube into a plurality of separate lumens.

2. The multi-lumen catheter of claim 1, further comprising a number of grooves extending along the interior of the tube to guide insertion of the divider through the length of the tube.

3. The multi-lumen catheter of claim 1 further comprising a number of grooves extending longitudinally along the exterior of the tube to facilitate radial expansion of the tube.

4. The multi-lumen catheter of claim 1 wherein the divider has a polygonal cross-section.

5. The multi-lumen catheter of claim 4 wherein the divider has a hollow triangular cross-section, with the area within the divider defining an additional lumen for the catheter.

6. The multi-lumen catheter of claim 1 further comprising a series of raised protrusions extending outward along the sides of the divider to prevent collapse of the tube against the divider.

7. A method of inserting a multi-lumen catheter into a blood vessel, comprising:
   (a) inserting one end of an expandable tube through an opening in the wall of the blood vessel; and
   (b) inserting a divider from the distal end of the tube through the length of the tube, thereby dividing the tube into a plurality of separate lumens and causing the tube to radially expand and substantially seal the opening between the outside of the tube and the opening in the wall of the blood vessel.

8. The method of claim 7, wherein the tube is inserted into the blood vessel by means of a hollow needle into which one end of the tube is inserted, and which is subsequently used to puncture the wall of the blood vessel.

9. The method of claim 7 wherein the divider has a polygonal cross-section.

10. The method of claim 7 wherein the divider has a cross-sectional configuration from the group consisting of a Y-shape, a cross, or a star having at least five points.

11. The method of claim 7 wherein divider has a triangular cross-section.

12. The method of claim 7 wherein the divider has a formed lumen extending axially within the divider.

13. A method of inserting a multi-lumen catheter into a blood vessel, comprising:
   (a) inserting one end of an expandable tube through an opening in the wall of the blood vessel by means of a hollow needle into which one end of the tube is inserted, and which is subsequently used to puncture the wall of the blood vessel; and
   (b) inserting a divider from the distal end of the tube through the length of the tube, thereby dividing the tube into a plurality of separate lumens.

14. A method of inserting a multi-lumen catheter into a blood vessel, comprising in the order of:
   (a) inserting one end of an expandable tube into a hollow needle;
   (b) inserting the needle through the wall of a blood vessel, so that the end of the tube inside the needle enters the blood vessel;
   (c) retracting the needle from the blood vessel and removing the needle from the tube, thereby leaving the end of the tube inside the blood vessel;
   (d) inserting a divider from the distal end of the tube through the length of the tube, thereby dividing the tube into a plurality of separate lumens.

15. The method of claim 14 wherein insertion of the divider into the tube causes the tube to radially expand, thereby substantially sealing the opening between the outside of the tube and the wall of the blood vessel.

16. The method of claim 14 wherein divider has a triangular cross-section.

17. The method of claim 16 wherein the divider has a hollow triangular cross-section, with the area within the divider defining a separate lumen.

18. The method of claim 14 wherein the needle has a slit extending its length through which the tube can be removed from inside the needle.

19. The method of claim 14 wherein the divider has a polygonal cross-section.

20. The method of claim 14 wherein the divider has a cross-sectional configuration from the group consisting of a Y-shape, a cross, or a star having at least five points.

21. The method of claim 14 wherein the divider has a formed lumen extending longitudinally with the divider.

22. The method of claim 14 wherein a number of grooves extending along the interior of the tube guide insertion of the divider through the length of the tube.

23. The method of claim 14 wherein a number of grooves extend longitudinally along the exterior of the tube to facilitate radial expansion of said tube as the divider is inserted.

24. The method of claim 14 wherein a series of raised protrusions extend outward from the divider to prevent collapse of the tube against the divider.

* * * * *